(12) United States Patent
Morita et al.

(10) Patent No.: US 8,574,492 B2
(45) Date of Patent: Nov. 5, 2013

(54) STERILIZATION-CLEANING DEVICE AND STERILIZATION-CLEANING METHOD FOR CAP

(75) Inventors: Yoshiyuki Morita, Yokohama (JP); Yoshinao Yamada, Yokohama (JP)

(73) Assignee: Toyo Seikan Kaisha, Ltd., Tokyo (JP)

(*) Notice: Subject to any disclaimer, the term of this patent is extended or adjusted under 35 U.S.C. 154(b) by 0 days.

(21) Appl. No.: 13/583,864

(22) PCT Filed: Feb. 22, 2011

(86) PCT No.: PCT/JP2011/053760
§ 371 (c)(1),
(2), (4) Date: Sep. 10, 2012

(87) PCT Pub. No.: WO2011/111513
PCT Pub. Date: Sep. 15, 2011

(65) Prior Publication Data
US 2013/0004368 A1    Jan. 3, 2013

(30) Foreign Application Priority Data
Mar. 10, 2010   (JP) .................................. 2010-53484

(51) Int. Cl.
*A61L 2/24* (2006.01)
(52) U.S. Cl.
USPC ............................................ 422/28; 134/131
(58) Field of Classification Search
USPC ................... 422/28; 134/25.4, 131
See application file for complete search history.

(56) References Cited

U.S. PATENT DOCUMENTS

| | | | |
|---|---|---|---|
| 3,833,339 A | 9/1974 | Pacilio | |
| 5,857,309 A * | 1/1999 | Cicha et al. | 53/167 |
| 2010/0275955 A1 | 11/2010 | Ueda et al. | |

FOREIGN PATENT DOCUMENTS

| | | |
|---|---|---|
| DE | 30 09 202 A1 | 9/1981 |
| JP | 48-100284 A | 12/1973 |
| JP | 2969120 B2 | 11/1999 |
| JP | 2001-341707 A | 12/2001 |
| JP | 3791868 B2 | 6/2006 |
| JP | 3969996 B2 | 9/2007 |
| JP | 2009-006215 A | 1/2009 |
| JP | 2009-154958 A | 7/2009 |
| WO | 2010/012334 A1 | 2/2010 |

OTHER PUBLICATIONS

English language machine translation of JP 2009-154958 A, published Jul. 2009, inventor: Ueda et al.*
International Search Report for PCT/JP2011/053760, mailing date of May 24, 2011.

* cited by examiner

*Primary Examiner* — Sean E Conley
(74) *Attorney, Agent, or Firm* — Westerman, Hattori, Daniels & Adrian, LLP

(57) ABSTRACT

Provided is a chute-type cap sterilization-cleaning device which transfers caps and performs sterilization-cleaning by injecting sterilization-cleaning liquid from a propulsion nozzle, wherein a controller (11) and a solenoid valve for controlling a plurality of reverse propulsion nozzles (2e) are provided, and wherein when sterilization and cleaning of a cap (C) is continued at a chute portion for sterilization-cleaning while cap transfer is stopped by a dividing device, in order to relax the accumulated pressure on the cap (C) at the downstream side, the reverse propulsion nozzles (2e) performing straight injection of the sterilization-cleaning liquid toward the reverse side with respect to the transfer direction of the cap (C) are arranged along the chute portion for sterilization-cleaning so that the injected flows are in contact with the inner surfaces of several caps (C).

2 Claims, 10 Drawing Sheets

STERILIZATION-CLEANING DEVICE AND STERILIZATION-CLEANING METHOD FOR CAP

TECHNICAL FIELD

The present invention relates to a cap sterilization-cleaning device, and in particular relates to a chute-type cap sterilization-cleaning device which obtains propulsive force for transferring caps simultaneously with sterilizing and cleaning the caps by continuous injection of a sterilization-cleaning liquid from a plurality of nozzles disposed along a chute, wherein even when the transfer of the caps is stopped during the operation of a propulsion nozzle, deformation of the caps in the chute can be favorably prevented.

BACKGROUND ART

In a sterile filling system such as an aseptic filling system, upon mounting a synthetic resin cap on a bottle (container) in which content such as a soft drink is filled, the cap is subject to sterilization and cleaning prior to supplying the cap to a capper. As cap sterilization-cleaning methods in the case, generally known are a method and a device for sterilizing and cleaning caps while transferring the caps in a chute based on their own weight (for instance, refer to Patent Document 1), and a method and a device for sterilizing and cleaning caps while transferring the caps in a turret or a drum-shaped star wheel (for instance, refer to Patent Documents 2 and 3).

With a chute-type sterilization-cleaning device, a cap transfer chute creates a transfer space with a plurality of rod-shaped guides disposed at least on the left, right, top and bottom in order to support the caps sideways to enable the cap to rotate, and the caps are transferred by passing through such transfer space. The caps transferred through the chute are sterilized and cleaned by injection of a sanitizer or aseptic water to the inner and outer surfaces of the caps from nozzles which are disposed at appropriate intervals on the left, right, top and bottom along the transfer passage. In many cases the sterilization-cleaning liquid is injected from the nozzles at an angle relative to the transfer direction so that the injected flow of the sterilization-cleaning liquid injected from the nozzles disposed along the chute is not obstruct the transfer of the caps.

Meanwhile, the present Applicant has previously devised and filed a patent application for a chute-type cap sterilization-cleaning device in which the chute transfer passage to be used in the sterilization-cleaning is configured in a rising slope so as to prevent deformation of the caps by relaxing the accumulated pressure working on the synthetic resin caps in the cap transfer chute, and enable the efficient sterilization-cleaning of the caps by reducing the influence of the warm water or aseptic water injected at the upstream side on the warm water or aseptic water on the downstream side (refer to Patent Document 4).

PRIOR ART

Patent Documents

Patent Document 1: Japanese Patent No. 2969120
Patent Document 2: Japanese Patent No. 3791868
Patent Document 3: Japanese Patent No. 3969996
Patent Document 4: Japanese Patent Application Publication No. 2009-154958

DISCLOSURE OF THE INVENTION

With the chute-type cap sterilization-cleaning device which obtains propulsive force for transferring caps simultaneously with sterilizing and cleaning the caps with the sterilization-cleaning liquid injected from the nozzles, there are advantages in that the system can be configured inexpensively comparison to a device which sterilizes and cleans the caps while transferring the caps by using power of a turret or the like since mechanical power is not required, and the space can be used efficiently since the transfer passage of the caps can be configured in the longitudinal direction (vertical direction).

Nevertheless, since a sanitizer is normally heated, during the sterilization process, the caps are transferred while being subjected to accumulated pressure in the chute and while being heated. A dividing device for controlling the transit time and processing speed is provided at the downstream of the chute. When the operation of this dividing device is halted, the caps are stopped in the chute transfer passage used for the sterilization-cleaning and are unable to push through the chute transfer passage. While it is desirable that the nozzles perform continuous injection in order to continuously perform the cap sterilization-cleaning, the caps are subject to accumulated pressure from the adjacent caps on either side while being heated. Consequently, there is a problem in that the cap skirt portion becomes deformed in an oval shape.

Thus, the present invention was devised in view of the problems of the conventional technology, and an object of this invention is to provide a chute-type cap sterilization-cleaning device which obtains propulsive force for transferring caps simultaneously with sterilizing and cleaning the caps by continuous injection of a sterilization-cleaning liquid from a plurality of nozzles disposed along a chute, wherein, even when the transfer of the caps is stopped during the operation of the propulsion nozzle, deformation of the caps in the chute can be favorably prevented.

Means for Solving Problem

In order to achieve the object, the cap sterilization-cleaning device of the present invention includes a chute and a dividing device in a cap transfer passage, a propulsion nozzle for injecting a sterilization-cleaning liquid to a plurality of caps in a transfer direction of the caps, a reverse propulsion nozzle for injecting the sterilization-cleaning liquid to the plurality of caps in a direction opposite to the transfer direction of the caps, a control unit for issuing a command to start injection by the reverse propulsion nozzle when the dividing device is stopped, and a control valve for issuing the command.

Moreover, with the cap sterilization-cleaning method of the present invention, when a plurality of caps to be sprayed with a sterilization-cleaning liquid which is injected in a cap transfer passage configured from a chute and a dividing device along a transfer direction of caps from propulsion nozzles are sprayed with the sterilization-cleaning liquid while the caps are stemmed due to stoppage of the dividing device, the sterilization-cleaning liquid is sprayed from a reverse propulsion nozzle to the caps in a direction opposite to a direction of transferring the caps.

Effects of the Invention

Even if the sterilization-cleaning liquid is sprayed from the propulsion nozzle and accumulated pressures are applied to the caps due to propulsive force when the dividing device is stopped, the cap sterilization-cleaning device and the sterilization-cleaning method of this invention can favorably inhibit the deformation of the caps by negating or weakening the accumulated pressure by spraying the sterilization-cleaning liquid to the caps also from the reverse propulsion nozzle.

Figure 1:
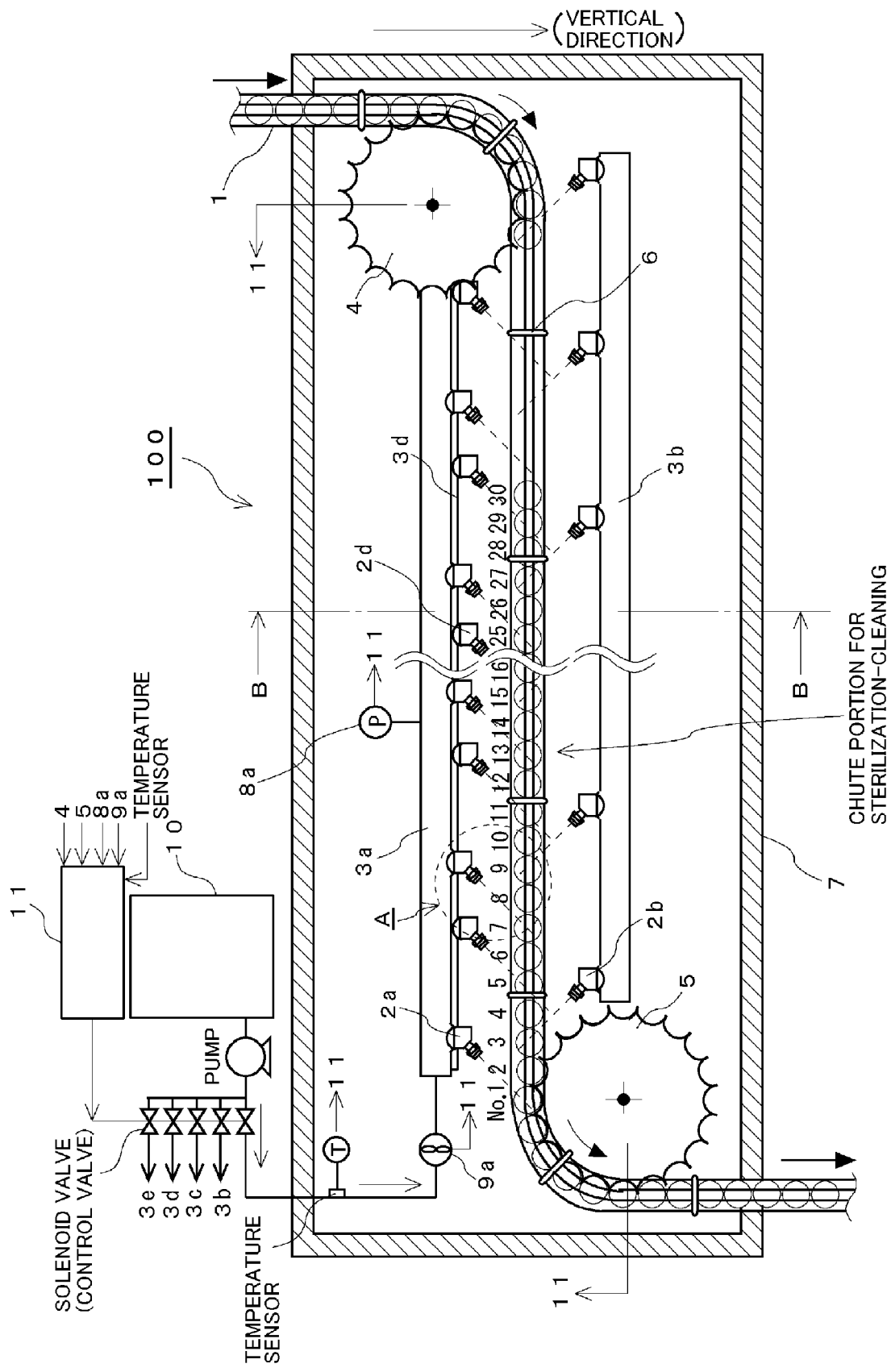
FIG. 1 is an explanatory drawing of the main part showing the cap sterilization-cleaning device of the present invention.

EXPLANATION OF REFERENCE NUMERALS 1 chute transfer passage
2a, 2b, 2c, 2d propulsion nozzle
2e reverse propulsion nozzle
3a, 3b, 3c, 3d propulsion supply pipe
3e reverse propulsion supply pipe
4 entrance side dividing device
5 exit side dividing device
6 chute transfer passage support member
7 chamber
8a, 8b, 8c, 8d, 8e pressure sensor
9a, 9b, 9c, 9d, 9e flow sensor
10 sterilization-cleaning liquid tank
11 controller
100 cap sterilization-cleaning device

BEST MODE FOR CARRYING OUT THE INVENTION

The present invention is now explained in further detail based on the embodiments shown in the drawings.

Figure 2:
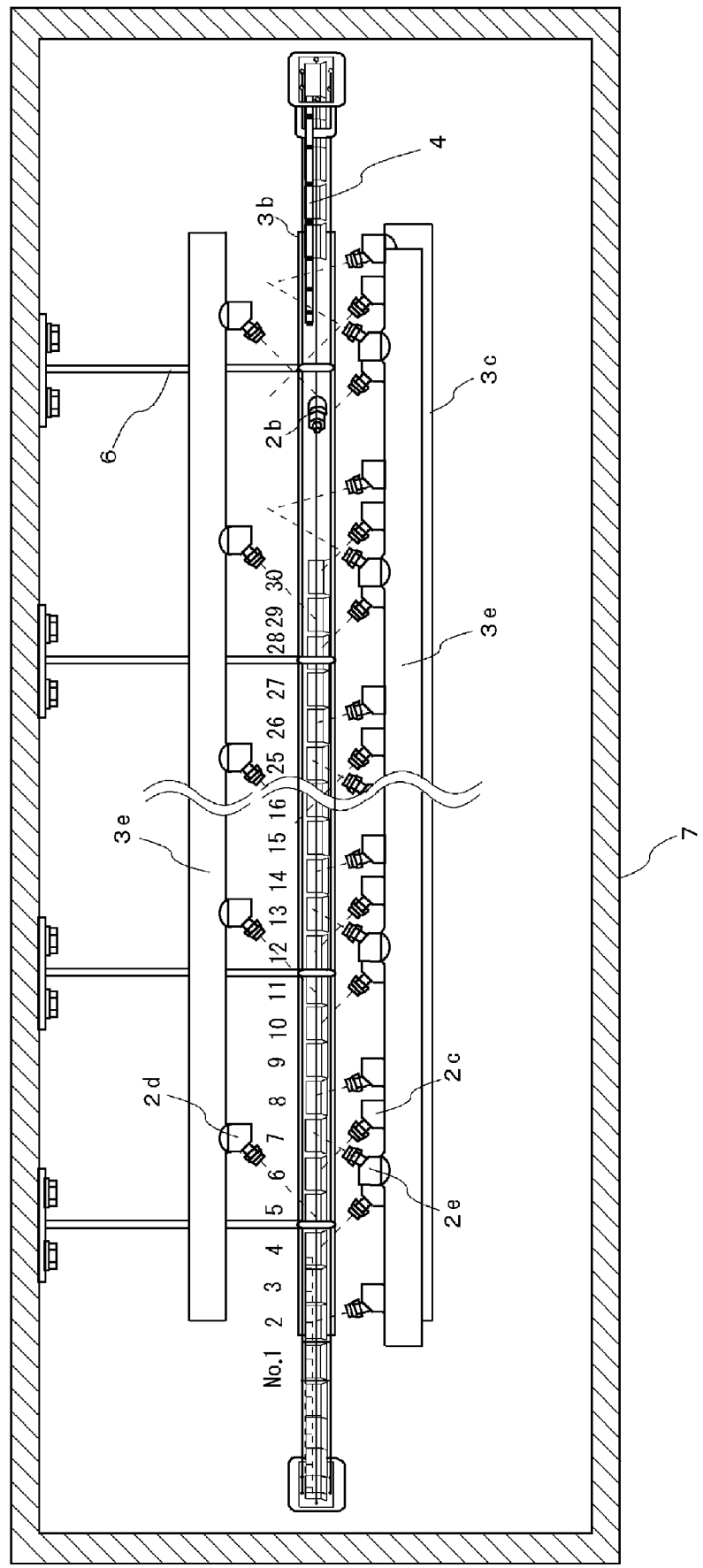
FIG. 2 is a plan view of the main part which shows FIG. 1 from above.

FIG. 1 is an explanatory drawing of the main part showing a cap sterilization-cleaning device 100 of the present invention. FIG. 2 is a plan view of the main part which shows FIG. 1 from above.

The cap sterilization-cleaning device 100 performs the sterilization-cleaning of the caps C by using propulsion nozzles 2a, 2b, 2c, 2d of different injection modes (injected flow center, intended target, intersection angle θ, divergence angle φ and the like described later), and additionally using a reverse propulsion nozzle 2e as needed.

The cap sterilization-cleaning device 100 can evenly sterilize and clean the caps C with a sterilization-cleaning liquid which is injected from the plurality of propulsion nozzles provided to the outer periphery of a pipe disposed along a chute transfer passage 1, and, without requiring a power mechanism such as a turret, stably transfer the caps C in the chute transfer passage 1 in a predetermined direction by using the force of the injected flow of the sterilization-cleaning liquid as the propulsive force. In addition, since the cap sterilization-cleaning device 100 additionally comprises a reverse propulsion nozzle which generates reverse propulsion force for negating or weakening the influence of the propulsive force, even if the dividing device is stopped while the sterilization-cleaning liquid is still being injected from the propulsion nozzles to the caps C and the plurality of caps C are consequently stemmed and backed up between the dividing devices, it is possible to relax the so-called crammed state where the plurality of caps are squeezed together and favorably inhibit the deformation of caps while continuing the sterilization-cleaning of caps by injecting the sterilization-cleaning liquid from the reverse propulsion nozzle to the caps C. Moreover, when the injected flow or temperature of the sterilization-cleaning liquid is unstable during the initial start-up or the restart of the cap sterilization-cleaning device, it is also possible to stop the transfer of the caps until the injected flow is stabilized by using the injection from the reverse propulsion nozzle, and thereby favorably preventing unstable sterilization-cleaning caused by an unstable injected flow.

As the configuration for realizing the above, the cap sterilization-cleaning device 100 is configured by mainly comprising a chute transfer passage 1 as the transfer passage of the caps C, an upper propulsion nozzle 2a, a lower propulsion nozzle 2b, a right propulsion nozzle 2c (refer to FIG. 2) and a left propulsion nozzle 2d for applying propulsive force for causing the caps C to advance in a predetermined direction along the chute transfer passage 1 based on the force of the injected flow of the sterilization-cleaning liquid simultaneously with injecting the sterilization-cleaning liquid to the caps C and sterilizing and cleaning an inner surface or an outer surface of the caps C, an upper propulsion supply pipe 3a, a lower propulsion supply pipe 3b, a right propulsion supply pipe 3c (refer to FIG. 2) and a left propulsion supply pipe 3d as pipes for supplying the sterilization-cleaning liquid to the "propulsion nozzles", a reverse propulsion nozzle 2e (refer to FIG. 2) for applying reverse propulsive force for causing the caps C to advance in a direction that is opposite to the transfer direction based on the force of the injected flow of the sterilization-cleaning liquid simultaneously with sterilizing and cleaning the inner surface or the outer surface of the caps C, a reverse propulsion supply pipe 3e (refer to FIG. 2) as a pipe for supplying the sterilization-cleaning liquid to the "reverse propulsion nozzle", an entrance side dividing device 4 for supplying the caps C at a predetermined time interval to a sterilization-cleaning zone where the caps C are sterilized and cleaned (range where the sterilization-cleaning liquid is sprayed in the chute transfer passage 1; hereinafter also referred to as the "sterilization-cleaning chute portion"), an exit side dividing device 5 for extracting the caps at the same time interval from the sterilization-cleaning chute portion in synch with the entrance side dividing device 4 and sending the caps C downstream, a chute transfer passage support member 6 for supporting the chute transfer passage 1, a chamber 7 for preventing the penetration of bacteria, dust and dirt and preventing the scattering of the sterilization-cleaning liquid, pressure sensors 8a, 8b, 8c, 8d, 8e (only 8a is shown in FIG. 1) for measuring the pressure (hereinafter referred to as the "injection pressure") of each of the supply pipes 3a, 3b, 3c, 3d, 3e, flow sensors 9a, 9b, 9c, 9d, 9e (only 9a is shown in FIG. 1) for measuring the flow rate of the sterilization-cleaning liquid which flows into each of the supply pipes 3a, 3b, 3c, 3d, 3e and temperature sensors (only the temperature sensor connected to the upper propulsion supply pipe 3a is shown in FIG. 1), a sterilization-cleaning liquid tank 10 and a pump for supplying the sterilization-cleaning liquid to each of the supply pipes 3a, 3b, 3c, 3d, 3e, and a controller 11 as a control unit for controlling the ON/OFF, via a solenoid valve as the control valve, the injection of the "propulsion nozzles" and the "reverse propulsion nozzle" based on a measurement signal of the pressure sensors and the flow sensors. Here, a flow regulating valve or a pressure regulating valve is preferably provided midway to the respective supply pipes 3a, 3b, 3c, 3d, 3e in addition to the solenoid valve so that the flow rate can be changed, but it is even more preferable to provide a proportional control valve to automatically control the flow rate of the respective supply pipes. In the case, the proportional control valve may be caused to function as the control valve in substitute for the solenoid valve. Furthermore, it is also preferable to provide a valving element so as to enable flow control and pressure control as needed regarding the respective propulsion nozzles and the reverse propulsion nozzle. As the sterilization-cleaning liquid, a medicinal solution, warm water or aseptic water may be used, and in this embodiment aseptic water (hereinafter referred to as the "warm water") of a temperature of, for example, 85° C. is used. Moreover, the operation of the controller 11 will be described later with reference to FIGS. 9 and 10. The respective configurations are now explained.

The chute transfer passage 1 is configured, for example, from six rod-shaped guiderails, and is a transfer space passage through which the caps C are passed internally. The shape of the chute transfer passage 1 is, for example, formed in a so-called crank shape of a vertical portion for lowering the caps C in a vertical direction as shown in FIG. 1→a horizontal portion for moving the caps C in a horizontal direction→and a vertical portion. In addition, since a gap is secured between the respective guiderails, it is possible to apply propulsive force to the caps C by spraying the sterilization-cleaning liquid injected from the propulsion nozzles to the caps C, and sufficiently sterilize and clean the inner surface or outer surface of the caps C while transferring the caps C. Moreover, since the transfer turret of the dividing devices 4, 5 can be inserted through the gap between the guiderails and place and cut the caps C which are being transferred in the pocket of the turret, it is also possible to maintain the transfer time (processing time) of the caps C to the intended value while maintaining the number of caps C (processing quantity) to the intended value (30 caps in this embodiment) in the sterilization-cleaning chute portion (horizontal portion) based on the dividing devices 4, 5. With the cap sterilization-cleaning device 100, while the sterilization-cleaning chute portion (horizontal portion) is configured in the form of one stage, the sterilization-cleaning chute portion (horizontal portion) may also be configured in a connected form in multiple stages via the dividing device or the vertical portion. Thereupon, while a horizontal portion that follows a preceding horizontal portion may be connected to the lower part of the preceding horizontal portion, it is also possible to dispose the caps so that the caps can be transferred upward via the dividing devices having a transfer drive force, and connect the following horizontal portion to the upper part of the preceding horizontal portion. Moreover, the vertical portion and horizontal portion may also be inclined and provided as a slope as needed. Furthermore, when the dividing devices do not need to be driven for transferring the caps, a simple open/close-type partition or the like may be used. Moreover, the dividing device may also be provided only to the horizontal portion or only to the vertical portion of the chute transfer passage.

The transfer force (propulsive force) of the caps C is mainly gravity in the vertical portion of the chute transfer passage 1, but the force (head) of the injected flow of each sterilization-cleaning liquid injected from each of the propulsion nozzles 2a, 2b, 2c, 2d becomes the main propulsive force in the horizontal portion (sterilization-cleaning chute portion). The transfer posture of the caps C in the chute transfer passage 1 is preferably a sideways posture where the opening of the caps C is facing sideways as shown in the drawing since it is also possible to reduce the loss of propulsive force by rolling and transferring the caps C.

Moreover, in this drawing, the caps C are rightly aligned in a state of preferably coming into contact with the injected flow from the respective nozzles. In addition, the numbers indicated along the sterilization-cleaning chute portion of the chute transfer passage 1 are the numbers (Nos.) for explaining the (relative) position of the caps C in the sterilization-cleaning chute portion which are the target (intended target) of the injected flow center of the nozzles 2a, 2b, 2c, 2d, 2e. In the drawing, for example, the injected flow center of the upper propulsion nozzle 2a is targeting the respective caps C of No. 1, No. 7, No. 13, . . . , No. 25. Moreover, as the number increases, this shows that the caps C are positioned more on the upstream side (accordingly, as the number decreases, this shows that the caps C are positioned more on the downstream side). Moreover, the intended number of caps C in the sterilization-cleaning chute portion was set to 30. Accordingly, numbers 1 to 30 are given to the caps C.

While the details are described later, the cap sterilization-cleaning device 100 sterilizes and cleans the inner surface and outer surface of the caps C by normally using four types of propulsion nozzles 2a, 2b, 2c, 2d. In this embodiment, in order to evenly sterilize all caps C in the sterilization-cleaning chute portion and to clean these caps by means of the nozzles, the respective propulsion nozzles are provided to the outer periphery of the supply pipe such that, with the respective injected flow centers not being overlappingly directed to a single cap, the sterilization-cleaning liquid from one propulsion nozzle is injected to a single cap C. Moreover, in this embodiment, the number of caps C secured in the sterilization-cleaning chute portion is 30, and, as the respective nozzles to spray the sterilization-cleaning liquid to the 30 caps C, a total of 30 propulsion nozzles; namely, five upper propulsion nozzles 2a, five lower propulsion nozzles 2b, fifteen right propulsion nozzles 2c, and five left propulsion nozzles 2d are used for sterilizing and cleaning the caps C.

As the propulsive force for the caps C that were cut from the entrance side dividing device 4 to reach the position of No. 30, the number of propulsion nozzles is preferably increased as needed as shown in the drawing, but it is also possible to use or arbitrarily adjust (for instance, adjustment for intermittently increasing the rotating speed) the rotating speed of the entrance side dividing device, or incline the chute to slope downward toward the outer side.

Figure 3:
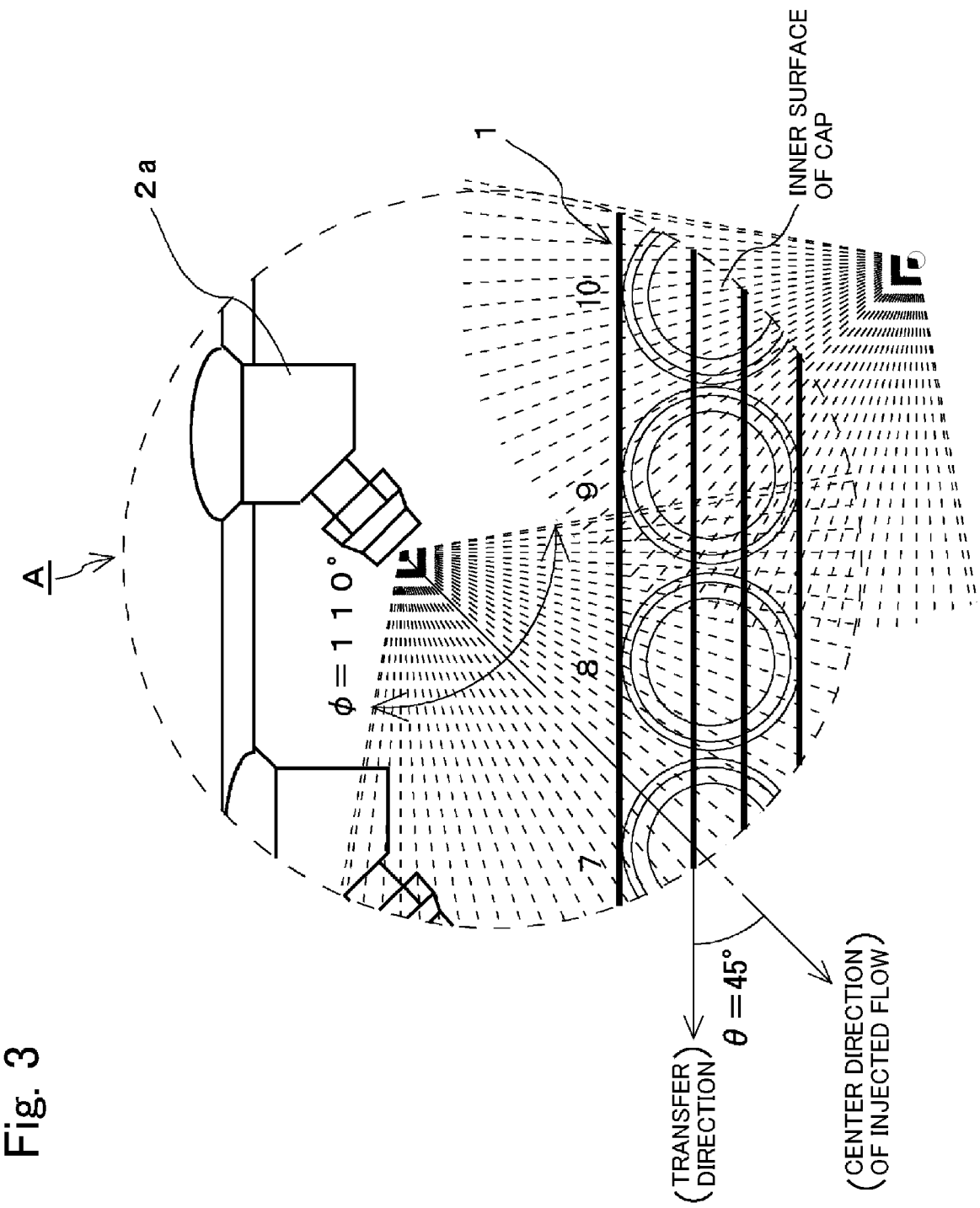
FIG. 3 is an enlarged drawing of portion A of FIG. 1.

The respective propulsion nozzles and the reverse propulsion nozzle are provided to the outer periphery of the supply pipe provided parallel to the sterilization-cleaning chute portion, and disposed so that the injected flow center thereof forms a predetermined intersection angle $\theta$ relative to the transfer direction of the caps C, or, in addition to the predetermined intersection angle $\theta$, so as to inject the sterilization-cleaning liquid at an injection mode of a predetermined divergence angle $\phi$ relative to the injected flow center. In this embodiment, the upper propulsion nozzle 2a and the lower propulsion nozzle 2b are disposed to have an intersection angle $\theta=45°$ and a divergence angle $\phi=110°$ relative to the cap transfer direction. Moreover, the right propulsion nozzles 2c are disposed such that there are those having an intersection angle $\theta=45°$ and a divergence angle $\phi=110°$ relative to the cap transfer direction, and those having an intersection angle θ=75° and a divergence angle φ=0° (mode of injection with hardly any spreading which is straightly injected along the injected flow center). Moreover, the left propulsion nozzle 2d is disposed to have an intersection angle θ=45° and a divergence angle φ=110° relative to the cap transfer direction. Moreover, the reverse propulsion nozzle 2e is disposed to have an intersection angle θ=120° and a divergence angle φ=0° relative to the cap transfer direction. The term "intersection angle θ" as used herein refers to, as shown in FIG. 3, an angle that is formed by the injected flow center and the cap transfer direction (advancing direction), and the term "divergence angle φ" refers to the center angle when the injected flow is approximated as a fan shape. In Tables 1, 3, and 5 described later, the straight injection of divergence angle φ=0° is indicated as "S", and the fan-shaped injection in which the divergence angle φ is not 0 degrees is indicated as "F".

The respective supply pipes 3a, 3b, 3c, 3d, 3e are provided along the sterilization-cleaning chute portion, and simultaneously supply the sterilization-cleaning liquid (warm water in this embodiment) to the respective propulsion nozzles 2a, 2b, 2c, 2d and the reverse propulsion nozzle 2e disposed at the outer periphery thereof. Moreover, the warm water is pressure-fed from an upstream sterilization-cleaning liquid tank 10 via the pump. In order to stabilize the injected flow from the respective propulsion nozzles 2a, 2b, 2c, 2d and the reverse propulsion nozzle 2e, the respective injection pressures of the respective supply pipes 3a, 3b, 3c, 3d, 3e are retained at a suitable constant pressure (for example, 0.1 to 0.3 [MPa]) by a publicly known pressure control mechanism (for instance, a pressure regulating valve or a relief valve, and in this embodiment a pressure regulating valve not shown in the drawing and provided respectively between the inlets of the respective supply pipes from the respective solenoid valves). In this embodiment, while the respective supply pipes 3a, 3b, 3c, 3d, 3e are of a tube shape, there is no limitation in the shape thereof so as long as the respective nozzles 2a, 2b, 2c, 2d, 2e can be provided at the outer periphery thereof along the sterilization-cleaning chute portion, and the pressure control mechanism can also be provided. Moreover, in substitute for the supply pipes, the propulsion nozzles and the reverse propulsion nozzle may also be piped and connected in a manner of being branched from the solenoid valve for turning ON/OFF the opening and closing of the respective nozzles.

The dividing devices 4, 5 include a pocket at the outer periphery of the wheel as a transfer turret where the caps C enter, and in this embodiment the dividing devices 4 and 5, in mutual synchronization, send the caps C to the sterilization-cleaning chute portion at a predetermined time interval (processing time) and simultaneously send the same number of caps C that have been sterilized and cleaned from the sterilization-cleaning chute portion toward the downstream side. Accordingly, the number of caps C (processing quantity) that is secured in the sterilization-cleaning chute portion by the dividing devices 4, 5 is always kept constant. Moreover, the dividing devices 4, 5 keep the sterilization-cleaning time (processing time) constant by also keeping constant the processing quantity per unit time in the sterilization-cleaning chute portion of the caps C. For example, in this embodiment, while the number of caps C retained in the sterilization-cleaning chute portion is 30, when the processing quantity (sending speed of the exit side dividing device) of the caps C is 600 caps per minute (=600 CPM), the sterilization-cleaning time is 30 caps/(600(caps/minute)/60 seconds)=3 seconds; that is, excluding the time required to reach No. 30, the inner surface and outer surface of the caps C are sterilized and cleaned evenly in 3-second intervals with warm water of 85° C.

Moreover, the pressure sensors 8a, 8b, 8c, 8d, 8e and the flow sensors 9a, 9b, 9c, 9d, 9e are used for determining whether the propulsion nozzles 2a, 2b, 2c, 2d and the reverse propulsion nozzle 2e are operating or stopped by confirming whether at least one value of either the pressure or flow rate has reached a predetermined value (range) (details will be explained later with reference to FIGS. 9 and 10).

The sterilization-cleaning liquid tank 10 stores, for example, warm water pre-heated to 85° C., and, by opening (turning ON) the respective solenoid valves blocking the passage between the sterilization-cleaning liquid tank 10 and the respective supply pipes 3a, 3b, 3c, 3d, 3e, the warm water is pressure-fed to the respective supply pipes 3a, 3b, 3c, 3d, 3e by a pump, and the warm water can thereby be injected from the respective nozzles 2a, 2b, 2c, 2d, 2e to the caps C based on the respective injection modes. Moreover, the warm water can also be prepared by heating aseptic water of ordinary temperature using a heating means such as a boiler.

The controller 11 controls the collection of angle information (for instance, publicly known rotary encoder signals) and the operation of the respective turrets of the dividing devices 4, 5, and controls the injection of each of the propulsion nozzles 2a, 2b, 2c, 2d and the reverse propulsion nozzle 2e based on each piece of sensor information of the pressure sensors 8a, 8b, 8c, 8d, 8e and the flow sensors 9a, 9b, 9c, 9d, 9e. Moreover, the start/stop of the injection of the respective nozzles is performed, for instance, by opening (turning ON)/closing (turning OFF) the solenoid valve on the downstream side of the sterilization-cleaning liquid tank 10.

Figure 4:
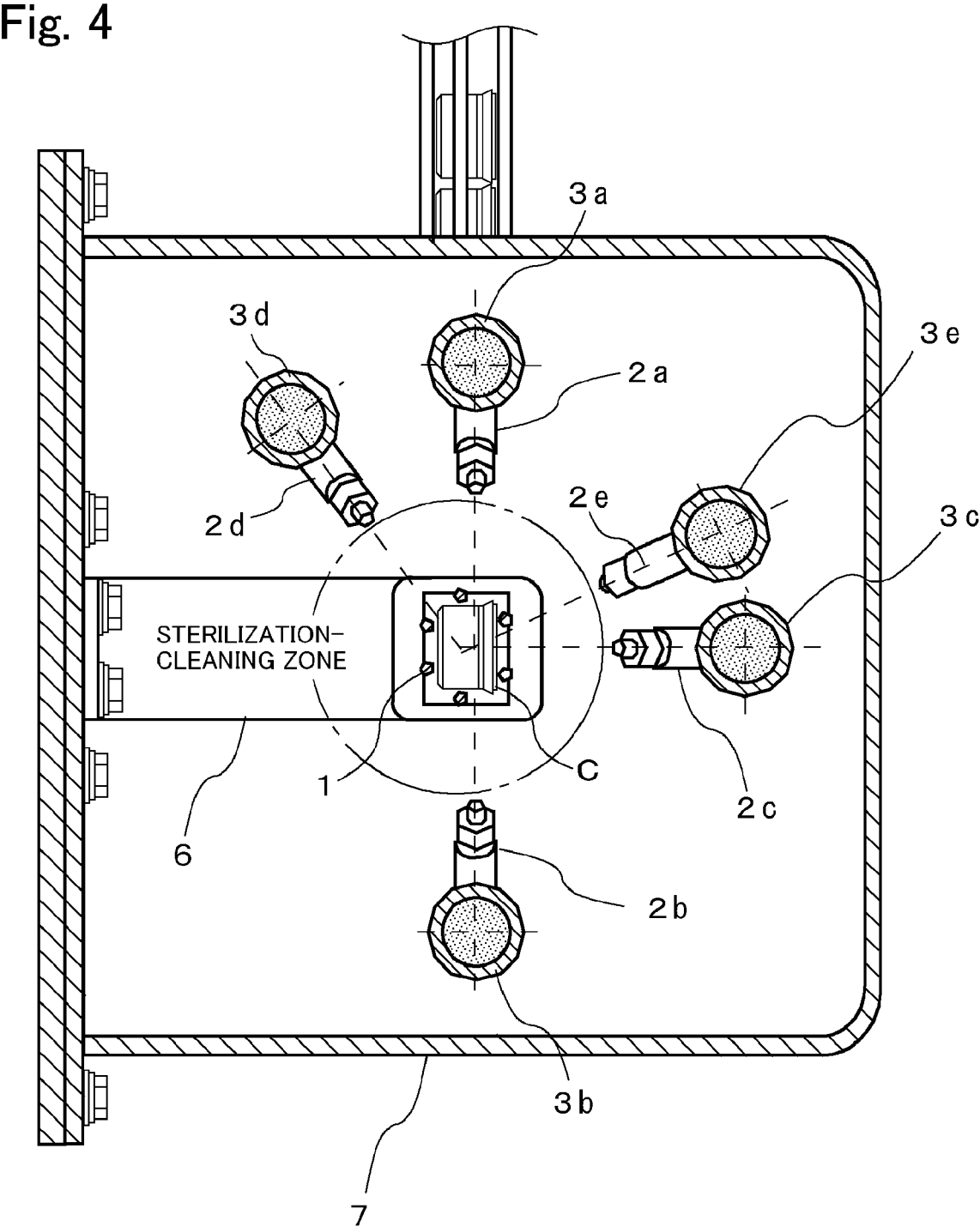
FIG. 4 is a cross section of line B-B of FIG. 1 according to the present invention.

FIG. 4 is a cross section of line B-B of FIG. 1, and is an explanatory drawing showing the relative positional relationship of the "propulsion nozzle" and "reverse propulsion nozzle" relative to the cap C. In this embodiment, the upper propulsion nozzle 2a and the lower propulsion nozzle 2b sterilize and clean the outer periphery (outer surface) of the body of the caps C, the left propulsion nozzle 2d sterilizes and cleans the outer surface of the top of the caps C, and the right propulsion nozzle 2c and the reverse propulsion nozzle 2e sterilize and clean the inner periphery (inner surface) of the caps C. For the sake of convenience in illustration, while it is illustrated as though the respective injected flow centers of the respective nozzles are colliding with the same cap C, as shown in Tables 1, 3, and 5 in following pages, preferably the respective injected flow centers of the respective nozzles belonging to the "propulsion nozzles" do not collide with the same cap. In this embodiment, the respective nozzles 2a, 2b, 2c, 2d belonging to the "propulsion nozzles" are disposed along the sterilization-cleaning chute portion so as to inject the warm water to mutually different caps C in a one-to-one mode without overlapping with each other. Meanwhile, only the caps C (for instance, the respective caps C of No. 7, No. 13, No. 19, and No. 25 in Table 1) to receive (to be exposed to) the injected flow of the reverse propulsion nozzle 2e among the caps C simultaneously receive two injected flows of the "propulsion nozzles" and the "reverse propulsion nozzle" during the temporary stop processing explained later.

Table 1 shows the injection in the respective caps of each of the propulsion nozzles and the reverse propulsion nozzle according to the present invention.

In this embodiment, the upper propulsion nozzle 2a injects the respective caps C of No. 1, No. 7, No. 13, No. 19, and No. 25 as the intended target (target) in a fan shape mode where the intersection angle θ=45° and the divergence angle φ=110°. Moreover, the lower propulsion nozzle 2b injects the respective caps C of No. 3, No. 9, No. 15, No. 21, and No. 27 as the target in a fan mode shape where the intersection angle θ=45° and the divergence angle φ=110°. Moreover, the left propulsion nozzle 2d injects the respective caps C of No. 5, No. 11, No. 17, No. 23, and No. 29 as the target in a fan mode shape where the intersection angle θ=45° and the divergence angle φ=110°. Meanwhile, the right propulsion nozzle 2c injects the respective caps C of No. 2, No. 4, No. 6, No. 8, No. 10, No. 12, No. 14, No. 16, No. 18, No. 20, No. 22, No. 24, No. 26, No. 28, and No. 30 as the target, but injects the respective caps C of No. 2, No. 8, No. 14, No. 20, and No. 26 in a straight mode where the intersection angle θ=75° and the divergence angle φ=0°. Moreover, when the caps C of No. 8, No. 14, No. 20, and No. 26 are respectively used as the "reference cap" among the caps to become the target of the nozzles where the divergence angle φ=0° among the caps to become the target of the right propulsion nozzle 2c, the reverse propulsion nozzle 2e injects caps C which are respectively one on the downstream side relative to the reference caps in a straight mode where the intersection angle θ=120° and the divergence angle φ=0°. (It is also possible to use No. 2 as a reference cap and cause the injected flow of the reverse propulsion nozzle 2e to also come into contact with the cap of No. 1, but in this embodiment, the caps near the exit side dividing device 5 have a low degree of contribution to the relaxation of the accumulated pressure and have thereby been omitted.) Moreover, the intersection angle θ and the divergence angle φ are merely an example, and the setting range is normally intersection angle: 0<θ<180° and divergence angle: 0≤φ≤120° depending on the sterilization-cleaning conditions and other matters. In particular, while the intersection angle of the propulsion nozzles is 0<θ<90° (transfer direction side of the caps), the intersection angle of the propulsion nozzles is preferably 10°≤θ≤80°, and more preferably 30°≤θ≤50°. Moreover, while the intersection angle of the reverse propulsion nozzle is 90°<θ<180° (side that is opposite to the transfer direction of the caps), the intersection angle of the reverse propulsion nozzle is preferably 105°≤θ≤150° because it is difficult to obtain sufficient reverse propulsive force when θ<105°, and the disposition of the reverse propulsion nozzle is difficult when θ>150°. In order to obtain more sufficient reverse propulsive force and increase the freedom of disposing the reverse propulsion nozzle, 115°≤θ≤140° is more pref-erable. Moreover, the intersection angle θ of the respective nozzles 2a to 2e connected to the pipes 3a to 3e maybe changed arbitrarily without setting it to a fixed angle so as long as such intersection angle θ falls within a range where the propulsion nozzles and the reverse propulsion nozzle can fulfill their predetermined roles (in this embodiment, 2a to 2d are 0°<θ<90° with the propulsion nozzles, and 2e is 90°<θ<180° with the reverse propulsion nozzle). For example, the setting may also be such that the intersection angle θ increases or decreases as the cap position moves downstream so that the intersection angle θ is deformed linearly according to the cap position. The reverse propulsion nozzle 2e can yield greater reverse propulsion force by directing the injected flow to come into contact with the side wall of the inner surface of the cap on the upstream side when the caps are arranged as shown in FIG. 1.

In addition to the propulsion nozzles and the reverse propulsion nozzle, it is also possible to comprise a sterilization-cleaning liquid injection nozzle of θ=90° which does not belong to either of the propulsion nozzles and the reverse propulsion nozzle.

TABLE 1

| | | Relationship of Cap Position and Injection Nozzle | | | | | | | | | | | | | | |
|---|---|---|---|---|---|---|---|---|---|---|---|---|---|---|---|---|
| Cap No. | | 1 | 2 | 3 | 4 | 5 | 6 | 7 | 8 | 9 | 10 | 11 | 12 | 13 | 14 | 15 |
| Injection Nozzle No. | 2a | F | — | — | — | — | — | F | — | — | — | — | — | F | — | — |
| | 2b | — | — | F | — | — | — | — | — | F | — | — | — | — | — | F |
| | 2c | — | S1 | — | F | — | F | — | S1 | — | F | — | F | — | S1 | — |
| | 2d | — | — | — | — | F | — | — | — | — | — | F | — | — | — | — |
| | 2e | — | — | — | — | — | — | — | S2 | — | — | — | — | — | S2 | — |

| | | Relationship of Cap Position and Injection Nozzle | | | | | | | | | | | | | | |
|---|---|---|---|---|---|---|---|---|---|---|---|---|---|---|---|---|
| Cap No. | | 16 | 17 | 18 | 19 | 20 | 21 | 22 | 23 | 24 | 25 | 26 | 27 | 28 | 29 | 30 |
| Injection Nozzle No. | 2a | — | — | — | F | — | — | — | — | F | — | — | — | — | — | — |
| | 2b | — | — | — | — | — | F | — | — | — | — | — | F | — | — | — |
| | 2c | F | — | F | — | S1 | — | F | — | F | — | S1 | — | F | — | F |
| | 2d | — | F | — | — | — | — | — | F | — | — | — | — | — | F | — |
| | 2e | — | — | — | S2 | — | — | — | — | — | S2 | — | — | — | — | — |

F: Intersection angle 45° + divergence angle 110°
S1: Intersection angle 75° + divergence angle 0°
S2: Intersection angle 120° + divergence angle 0°
Reference cap Nos.: No. 8, No. 14, No. 20, No. 26

In summary, the upper propulsion nozzle 2a targets, in the fan shape mode (F), the outer surface of the cap body of cap Nos. 6n−5 (n is an integer of 1 to 5), the lower propulsion nozzle 2b targets, in the fan shape mode, the outer surface of the cap body of cap Nos. 6n−3 (n is an integer of 1 to 5), the right propulsion nozzle 2c injects, in the straight mode (S1), the inner surface of cap Nos. 6n−4 (n is an integer of 1 to 5), and injects, in the fan shape mode (F), the inner surface of cap Nos.=6n−2 and cap Nos. 6n (n is an integer of 1 to 5).

The left propulsion nozzle 2d targets, in the fan shape mode (F), the outer surface of the cap top of cap Nos. 6n−1 (n is an integer of 1 to 5), and the reverse propulsion nozzle 2e targets, in the straight mode (S2), the inner surface of cap Nos. 6n+1 (n is an integer of 1 to 4) adjacent to the downstream side of the reference caps when cap Nos. 6n+2 are used as the "reference cap".

Figure 5:
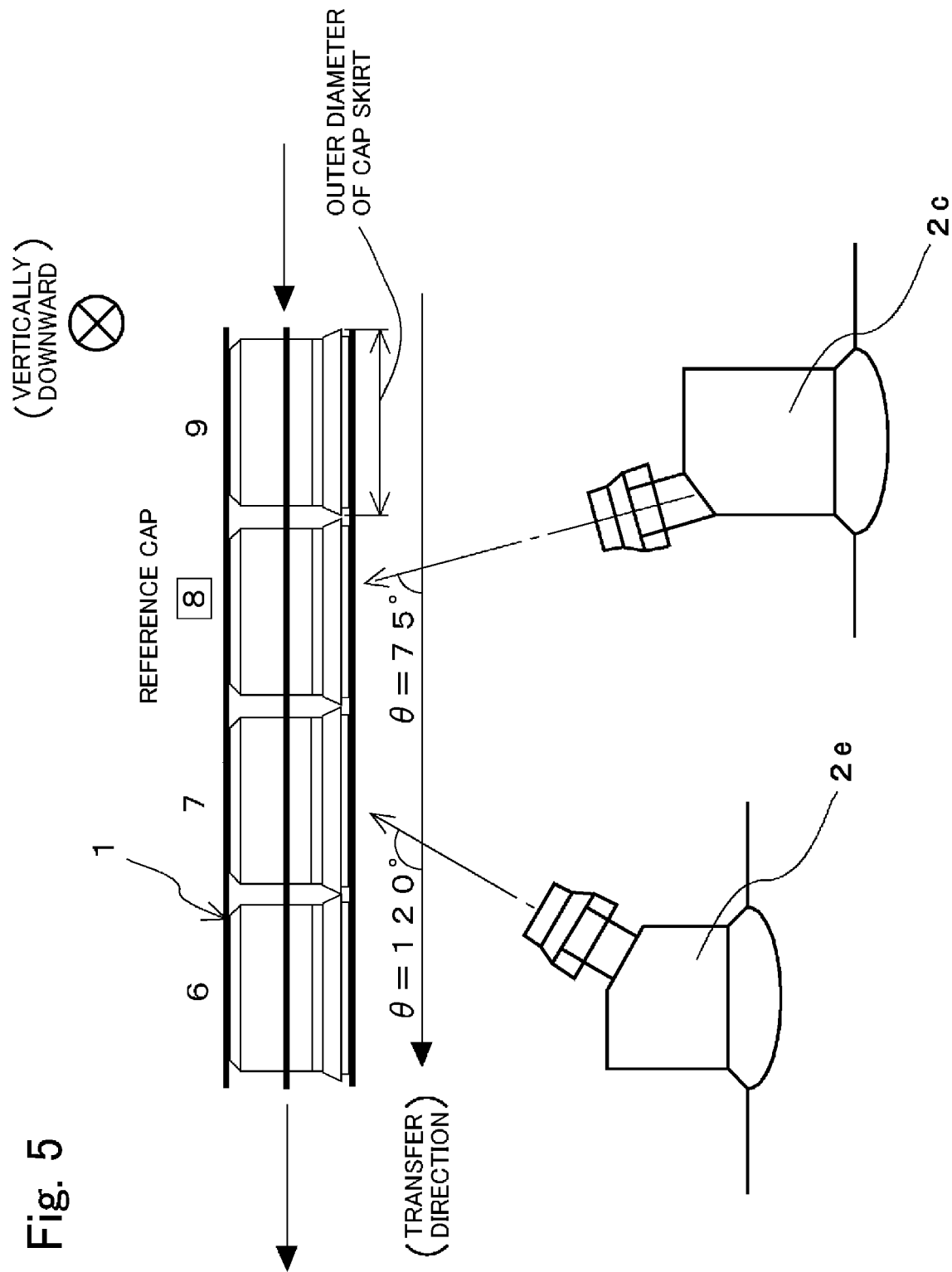
FIG. 5 is an explanatory drawing showing the injection of the nozzle of the present invention.

Table 2 shows the maximum value of ovality of the respective caps C when the sterilization-cleaning liquid is injected to the caps C while a predetermined 30 caps C are retained and the dividing devices 4, 5 are stopped in the respective sterilization-cleaning chute portions of the conventional technology and the present invention. The term "ovality" refers to the amount showing the difference between the maximum value of the outer diameter of a cap skirt and the minimum value of the outer diameter of the cap skirt shown in cap No. 9 of FIG. 5, and this ovality was used for defining the amount of deformation of the cap. Moreover, the smaller the ovality, the more relaxed the crammed state of the sterilization-cleaning chute portion. Table 2(a) shows the maximum value of ovality of the respective caps of the sterilization-cleaning chute portion in a case of not providing the reverse propulsion nozzle 2e as a comparative example; that is, in the sterilization-cleaning chute portion that only comprises the propulsion nozzle and does not include the reverse propulsion nozzle 2e in Table 1, and Table 2(b) shows the maximum value of ovality of the caps in the sterilization-cleaning chute portion comprising each of the propulsion nozzle and the reverse propulsion nozzle according to the present invention. Moreover, the reverse propulsion nozzle 2e was disposed so that the warm water can be injected to the inner surface of the cap C which is one downstream relative to the cap C (reference cap No. 8 in FIG. 5) targeted by the right propulsion nozzle 2c as shown in detail in FIG. 5, and the reverse propulsion nozzle 2e was also disposed so that the warm water can similarly be sprayed to the inner surface of the caps C of No. 13, No. 19, and No. 25 which are one downstream of the other reference cap Nos. 14, No. 20, and No. 26. Moreover, the stop time (injection time) in the sterilization-cleaning chute portion was set to "stop time of 20 seconds", "stop time of 60 seconds", and "stop time of 180 seconds".

TABLE 2(a)

| | Stop time | | |
|---|---|---|---|
| | 20 seconds | 60 seconds | 180 seconds |
| Maximum value of ovality | 1.4 mm | 1.8 mm | 2.3 mm |

TABLE 2(b)

| | Stop time | | |
|---|---|---|---|
| | 20 seconds | 60 seconds | 180 seconds |
| Maximum value of ovality | 0.9 mm | 0.9 mm | 1.1 mm |

If the exit side dividing device 5 stops for some reason while the caps C are moving in the sterilization-cleaning chute portion while being sprayed with the warm water from the propulsion nozzles, the 30 caps C in the sterilization-cleaning chute portion continue to receive the propulsive force from the propulsion nozzles 2a, 2b, 2c, 2d and become a crammed state in a state where movement is restricted by the exit side dividing device 5 (while the caps C are affected by the drive force of the entrance side dividing device 4 if the entrance side dividing device 4 continues to operate, in order to simplify the explanation, the explanation continues as follows on the supposition that the entrance side dividing device 4 also stopped simultaneously with the stoppage of the exit side dividing device 5). In the case, the respective caps C are subject to the sum of propulsive forces of all caps C on the right side (upstream side) of itself from the cap C on the right side (adjacent on the upstream side), and, based on the principle of action and reaction, simultaneously be subject to the sum of propulsive forces from all caps C on the upstream side of itself, and, when that cap C is also receiving propulsive force by the injection of warm water from the propulsion nozzles, that cap C is also subject to force that is substantially equal to a value obtained by further adding such propulsive force from the cap C on the left side (adjacent on the downstream side) of itself. In other words, the respective caps C are placed in a state of continuously receiving the compressive load from the adjacent caps on the upstream side and the downstream side in a high-temperature state. The compressive load (hereinafter also referred to as the "accumulated pressure of the caps") increases from the upstream side toward the downstream side, and becomes maximum at the cap C of No. 1 if excluding the influence of the turret pocket of the exit side dividing device 4. Thus, with the cap sterilization-cleaning device 100, when the dividing devices 4, 5 are stopped, the warm water is injected from the reverse propulsion nozzle 2e based on the injection mode, and the reverse propulsion force caused by the injected flow of the warm water is used to negate or weaken the influence of the propulsive force and relax the accumulated pressure of the caps. If the reverse propulsion nozzles 2e are scattered at a plurality of locations as described above, that is preferable since the accumulated pressure of the caps can be effectively relaxed by reducing the force of injection of each reverse propulsion nozzle 2e and reduce the reverse propulsive force to be applied to one cap.

Based on Table 2(a), with the conventional cap sterilization-cleaning device only comprising the propulsion nozzles, the caps on the downstream side are subject to accumulated pressure as the stop time in the sterilization-cleaning chute portion is longer, and the amount of deformation of the cap increases. Meanwhile, with the cap sterilization-cleaning device 100 of the present invention, as a result of the accumulated pressure of the caps being preferably weakened, as shown in Table 2(b), while the amount of deformation of the caps increases slightly as the stop time increases, it can be understood that the difference in the amount of deformation of the cap in relation to the stop time is considerably smaller in comparison to the conventional cap sterilization-cleaning device.

Figure 6:
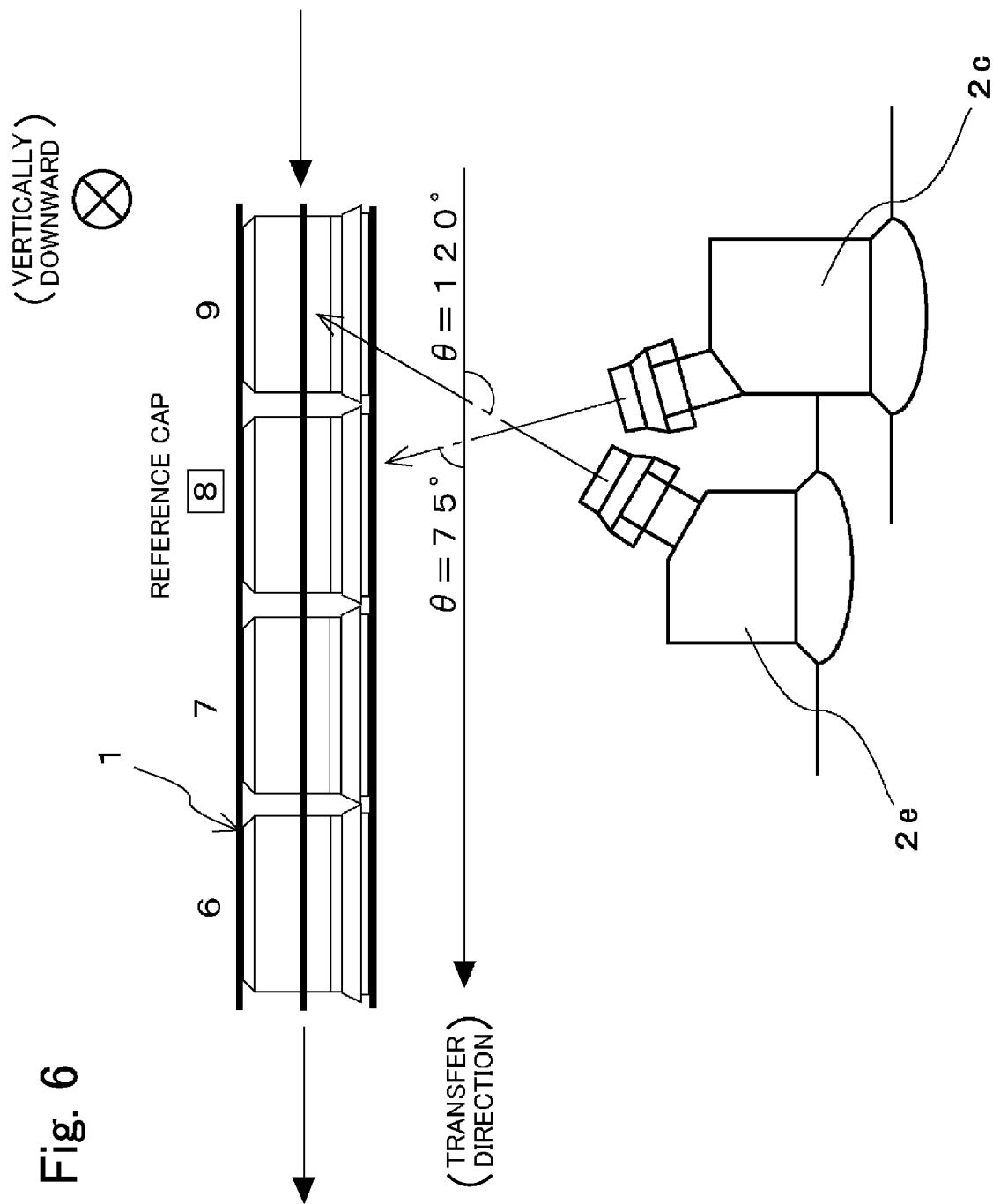
FIG. 6 is an explanatory drawing showing the injection of the reverse propulsion nozzle according to another embodiment of the present invention.

While the maximum value of ovality in the "stop time of 20 seconds" is 1.4 mm in conventional technology, the result was 0.9 mm in the present invention, while the maximum value of ovality in the "stop time of 60 seconds" is 1.8 mm in conventional technology, the result was 0.9 mm in the present invention, and while the maximum value of ovality in the "stop time of 180 seconds" is 2.3 mm in conventional technology, the result was 1.1 mm in the present invention FIG. 6 is an explanatory drawing showing the injection of the reverse propulsion nozzle according to another embodiment of the present invention.

Figure 8:
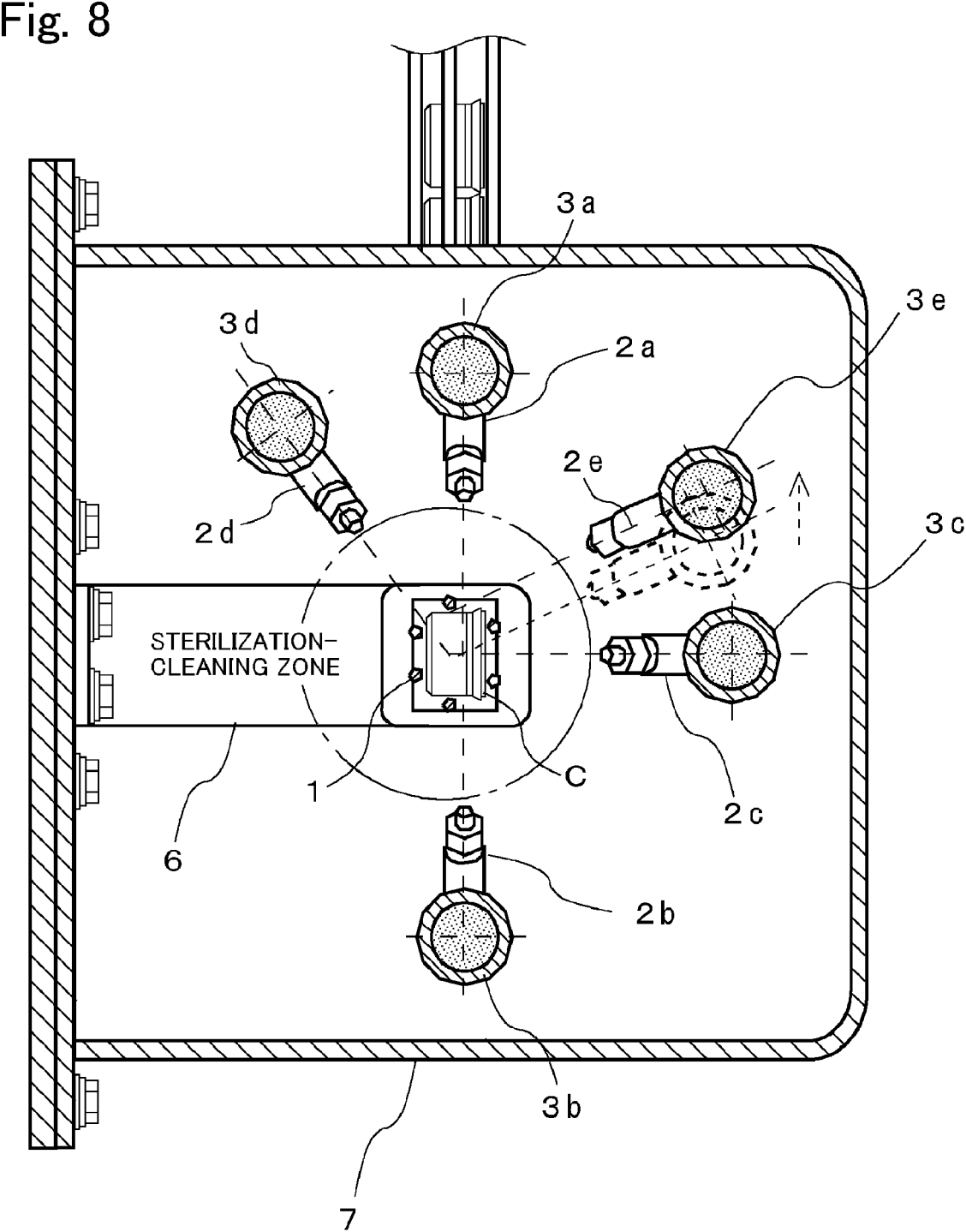
FIG. 8 is a cross section of line B-B of FIG. 1 according to another embodiment and to yet another embodiment of the present invention.

With respect to the injection of the reverse propulsion nozzle 2e, the right propulsion nozzle 2c is disposed so that it can linearly inject the sterilization-cleaning liquid, at an intersection angle $\theta=120°$ and a divergence angle $\phi=0°$, to the upper part of the outer surface of the body of the cap C that is one upstream as the target related to the targeted cap C (reference cap No. 8 in FIG. 6) (the other reverse propulsion nozzles 2e are also similarly disposed based on the reference caps No. 14, No. 20, and No. 26). The relationship of the respective cap positions and the respective injection nozzles in this case is shown in Table 3. The respective injection modes of the propulsion nozzles 2a, 2b, 2c, 2d are the same as Table 1. Moreover, the relationship of the caps C and the injection positions in the arrow view B-B of FIG. 1 is basically the same as the former embodiment and is as shown in FIG. 8. (The reverse propulsion supply pipe 3e and the reverse propulsion nozzle 2e were moved upward so that the injected flow of the reverse propulsion nozzle can more easily come into contact with the upper part of the outer surface of the body of the caps C.)

TABLE 3

| | | \multicolumn{15}{c}{Relationship of Cap Position and Injection Nozzle} |
|---|---|---|---|---|---|---|---|---|---|---|---|---|---|---|---|

| | Cap No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Injection Nozzle No. | 2a | F | — | — | — | — | — | F | — | — | — | — | — | F | — | — |
| | 2b | — | — | F | — | — | — | — | — | F | — | — | — | — | — | F |
| | 2c | — | S1 | — | F | — | F | — | S1 | — | F | — | F | — | S1 | — |
| | 2d | — | — | — | — | F | — | — | — | — | — | F | — | — | — | — |
| | 2e | — | — | — | — | — | — | — | — | S2 | — | — | — | — | — | S2 |

| | Cap No. | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| Injection Nozzle No. | 2a | — | — | — | F | — | — | — | — | — | F | — | — | — | — | — |
| | 2b | — | — | — | — | — | F | — | — | — | — | — | F | — | — | — |
| | 2c | F | — | F | — | S1 | — | F | — | F | — | S1 | — | F | — | F |
| | 2d | — | F | — | — | — | — | — | F | — | — | — | — | — | F | — |
| | 2e | — | — | — | — | S2 | — | — | — | — | — | S2 | — | — | — | — |

F: Intersection angle 45° + divergence angle 110°
S1: Intersection angle 75° + divergence angle 0°
S2: Intersection angle 120° + divergence angle 0°
Reference cap Nos.: No. 8, No. 14, No. 20, No. 26

Table 4 shows the maximum value of ovality of the 30 retained caps in the injection modes of Table 3. The respective maximum values of the cap ovality at the stop times of 20 seconds, 60 seconds, and 180 seconds in the injection modes were 1.0 [mm], 1.2 [mm], and 1.4 [mm].

TABLE 4

| | Stop time | | |
|---|---|---|---|
| | 20 seconds | 60 seconds | 180 seconds |
| Maximum value of ovality | 1.0 mm | 1.2 mm | 1.4 mm |

Figure 7:
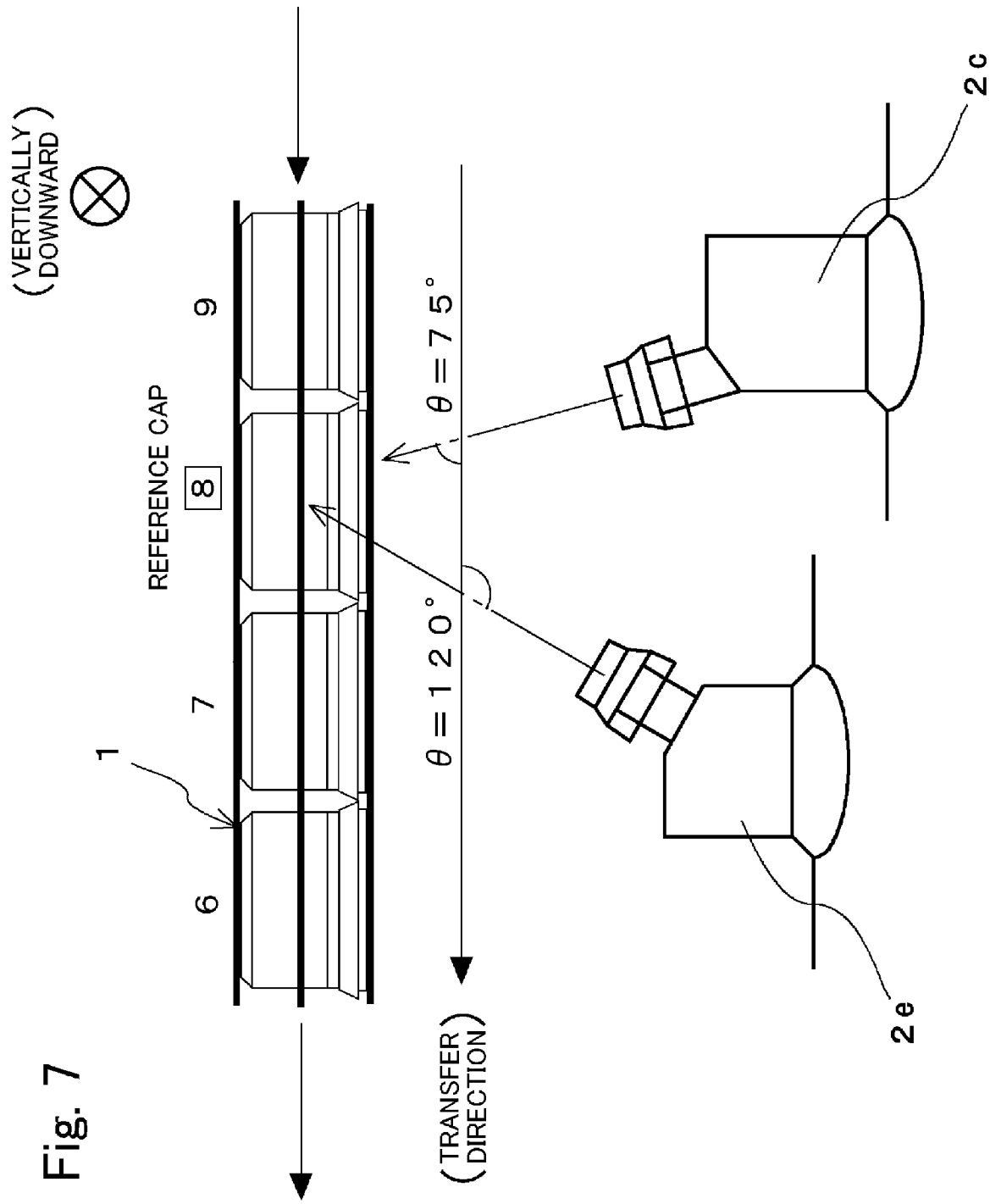
FIG. 7 is an explanatory drawing showing the injection of the reverse propulsion nozzle according to yet another embodiment of the present invention.

FIG. 7 is an explanatory drawing showing the injection of the reverse propulsion nozzle according to yet another embodiment of the present invention.

With respect to the injection of the reverse propulsion nozzle $2e$, the right propulsion nozzle $2c$ is disposed so that it can linearly inject the sterilization-cleaning liquid, at an intersection angle $\theta=120°$ and a divergence angle $\phi=0°$, to the upper part of the outer surface of the body of the same cap C as the target related to the targeted cap C (reference cap No. 8 in FIG. 7) (the other reverse propulsion nozzles $2e$ are also similarly disposed based on the reference caps No. 14, No. 20, and No. 26). The relationship of the respective cap positions and the respective injection nozzles in the case is shown in Table 5. The respective injection modes of the propulsion nozzles $2a$, $2b$, $2c$, $2d$ are the same as Table 1. Moreover, the relationship of the caps C and the injection positions in the arrow view B-B of FIG. 1 is as shown in FIG. 8.

TABLE 5

| | Cap No. | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Injection Nozzle No. | 2a | F | — | — | — | — | — | F | — | — | — | — | — | F | — | — |
| | 2b | — | — | F | — | — | — | — | — | F | — | — | — | — | — | F |
| | 2c | — | S1 | — | F | — | F | — | S1 | — | F | — | F | — | S1 | — |
| | 2d | — | — | — | — | F | — | — | — | — | — | F | — | — | — | — |
| | 2e | — | — | — | — | — | — | — | — | S2 | — | — | — | — | — | S2 |

| | Cap No. | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| Injection Nozzle No. | 2a | — | — | — | F | — | — | — | — | — | F | — | — | — | — | — |
| | 2b | — | — | — | — | — | F | — | — | — | — | — | F | — | — | — |
| | 2c | F | — | F | — | S1 | — | F | — | F | — | S1 | — | F | — | F |
| | 2d | — | F | — | — | — | — | — | F | — | — | — | — | — | F | — |
| | 2e | — | — | — | — | S2 | — | — | — | — | — | S2 | — | — | — | — |

F: Intersection angle 45° + divergence angle 110°
S1: Intersection angle 75° + divergence angle 0°
S2: Intersection angle 120° + divergence angle 0°
Reference cap Nos.: No. 8, No. 14, No. 20, No. 26

Table 6 shows the maximum value of ovality of the 30 caps in the injection modes of Table 5. The respective maximum values of the cap ovality at the stop times of 20 seconds, 60 seconds, and 180 seconds in the injection modes were 1.4 [mm], 1.4 [mm], and 1.4 [mm].

TABLE 6

|  | Stop time | | |
| --- | --- | --- | --- |
|  | 20 seconds | 60 seconds | 180 seconds |
| Maximum value of ovality | 1.4 mm | 1.4 mm | 1.4 mm |

Based on the above results, the amount of deformation of the caps was smallest with the injection of the nozzles of Table 1 among the injection of nozzles of Table 1, Table 3, and Table 5. It is considered that the reverse propulsion nozzle is effective in obtaining the reverse propulsion force when injected toward the inner surface side of the caps, and also considered effective in obtaining the reverse propulsive when injected linearly at a divergence angle $\phi=0°$. In addition, it is considered that ovality can be effectively inhibited by injecting warm water from the reverse propulsion nozzle to the adjacent cap that is one downstream (especially the adjacent cap that is one downstream of the reference cap) among the caps subject to high propulsive force by the propulsion nozzles (in the above embodiment, caps subject to the injected flow from the propulsion nozzle 2c having a divergence angle $\phi=0°$ among the propulsion nozzles 2c to inject warm water toward the inner surface side of the caps).

Figure 9:
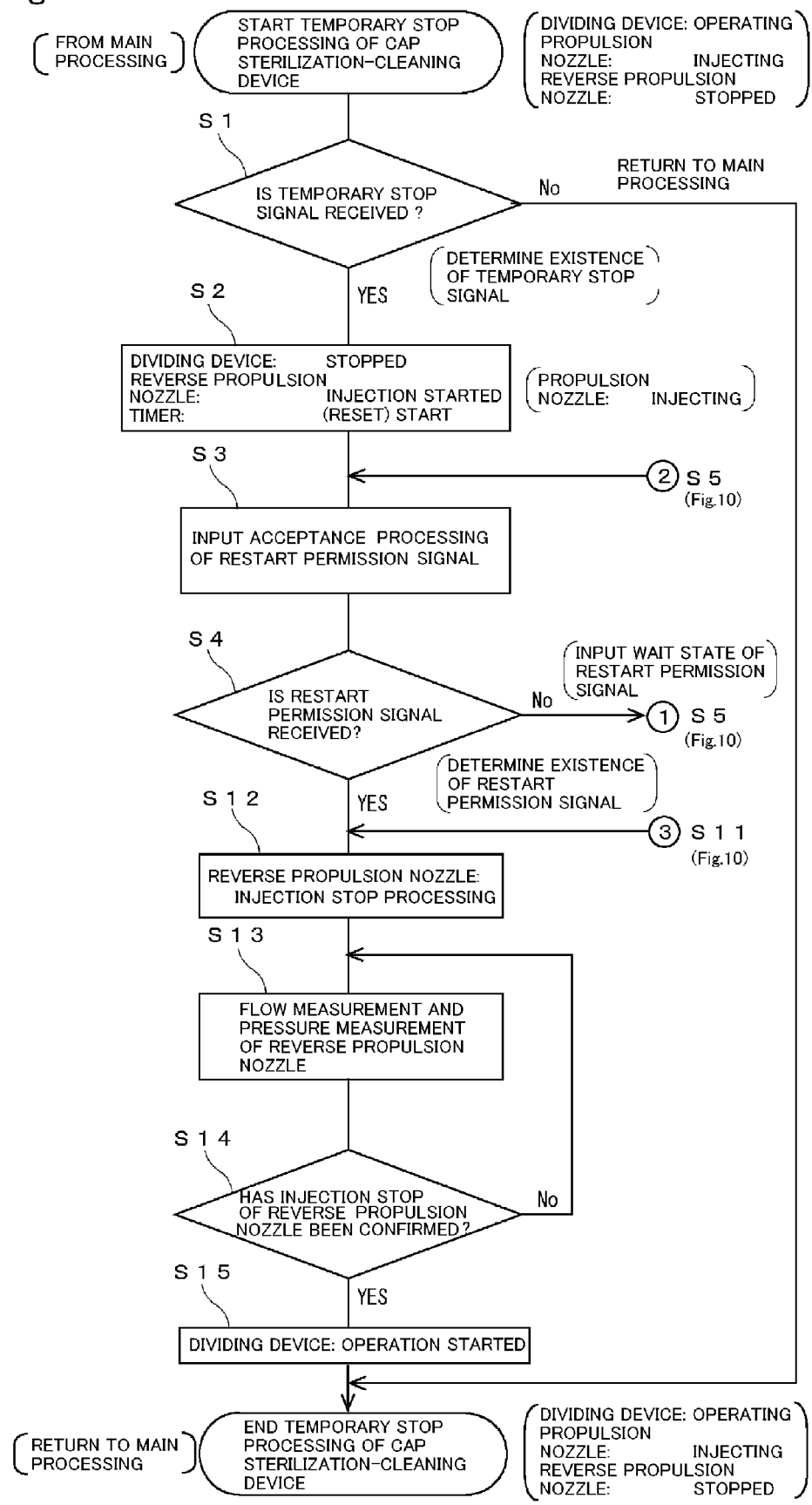
FIG. 9 is a flowchart of the main body part of the temporary stop processing of the cap sterilization-cleaning device.
Figure 10:
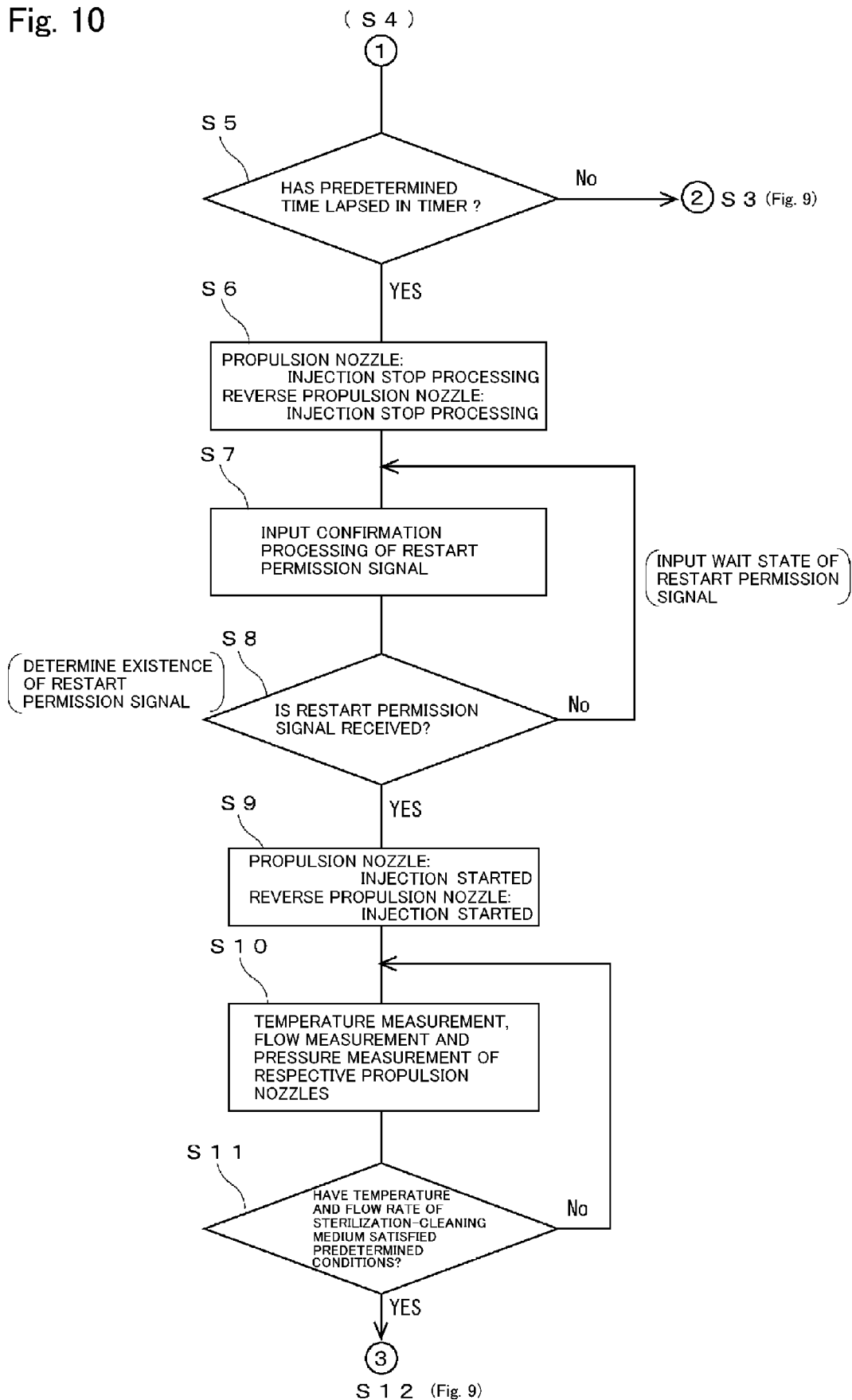
FIG. 10 is a flowchart of the branch part of the temporary stop processing of the cap sterilization-cleaning device.

FIGS. 9 and 10 are flowcharts of the "temporary stop processing of the cap sterilization-cleaning device" which mainly show, as an example of the nozzle injection control of the present invention, the command control of the propulsion nozzles 2a, 2b, 2c, 2d and the reverse propulsion nozzle 2e of the controller 11 upon restarting the operation of the cap cleaning apparatus from the ordinary operating state thereof and after going through a temporary stop.

The explanation starts with a state where the cap sterilization-cleaning device 100 which adopts the embodiment of FIGS. 1 to 5 described above and Table 1 is normally being operated. In other words, the dividing devices 4, 5 are being operated, warm water is being injected from the respective propulsion nozzles 2a, 2b, 2c, 2d toward the inner surface or outer surface of the caps C, and the caps C are being transferred to a predetermined direction. The reverse propulsion nozzle 2e is in a stopped state.

Foremost, from the main processing not shown in the drawing, the "temporary stop processing of the cap sterilization-cleaning device" of FIG. 9 is repeatedly called. In step S1, whether a temporary stop signal was received due to a command input operation or warning through use of a button by an operator is determined. When it is determined that the temporary stop signal was received (YES), the routine proceeds to step S2. When it is determined that the temporary stop signal was not received (No), the "temporary stop processing of the cap sterilization-cleaning device" is ended without performing any additional processing, and the routine returns to the main processing.

In step S2, the dividing devices 4, 5 are stopped and warm water is injected from the reverse propulsion nozzle 2e. By issuing a command for turning ON (opening) the solenoid valve that is blocking the passage between the sterilization-cleaning liquid tank 10 and the reverse propulsion supply pipe 3e, the solenoid valve is opened and the warm water is supplied to the reverse propulsion supply pipe 3e, and the warm water is injected from the reverse propulsion nozzle 2e toward the inner surface of the caps C. The caps C are in a state of continuously receiving the warm water from the respective propulsion nozzles 2a, 2b, 2c, 2d or the reverse propulsion nozzle 2e, and the transfer thereof is stopped.

Moreover, a timer for monitoring whether the stoppage is for a long time is preferably reset and started at this time.

In step S3, the restart permission signal of the cap cleaning apparatus 100 is accepted, and a restart enable command based on the operator's button operation or the like and a signal input based on restart enabling according to an all-clear signal is accepted.

Subsequently, in step S4, whether a restart permission signal was received is determined. When a restart permission signal was received (YES), the routine proceeds to step S11. When a restart permission signal was not received (No), this determination processing is repeated until a restart permission signal is received, but it is preferable to add processing for once stopping the propulsion nozzles and the reverse propulsion nozzle as shown in steps S5 to S11 of FIG. 10 in order to inhibit the wasteful consumption of energy and preventing abnormal deformation of caps when the stoppage extends over a long time.

In step S5 (FIG. 10), whether the predetermined time lapses the time that was set as a tolerable time from the perspective of inhibiting energy consumption and preventing abnormal deformation of caps is determined based on a value of the timer described above in step S2. When the time has not elapsed, the routine returns to the restart permission signal input acceptance processing of step S3 (FIG. 9), and when the time has elapsed, the routine proceeds to step S6.

In step S6, the respective solenoid valves connected between the sterilization-cleaning liquid tank 10 and the respective supply pipes 3a, 3b, 3c, 3d, 3e are turned OFF (closed) as the processing for stopping the injection of warm water of the respective propulsion nozzles 2a, 2b, 2c, 2d and the reverse propulsion nozzle 2e.

In subsequent steps S7 and S8, the input acceptance and reception determination of the restart permission signal similar to steps S3 and S4 described above are performed.

In step S8, when a restart permission signal is not received, the routine immediately returns to step S7.

Subsequently, in step S9, to prepare for the operation of the recovered cap cleaning apparatus, warm water is injected from the respective propulsion nozzles 2a, 2b, 2c, 2d and the reverse propulsion nozzle 2e. By turning ON (opening) the solenoid valves blocking the passage between the sterilization-cleaning liquid tank 10 and the respective supply pipes 3a, 3b, 3c, 3d, 3e, the warm water is supplied to the respective supply pipes 3a, 3b, 3c, 3d, 3e, and the warm water is simultaneously injected from the respective propulsion nozzles 2a, 2b, 2c, 2d and the reverse propulsion nozzle 2e toward the inner surface or outer surface of the caps C. The reason why the warm water to also be injected from the reverse propulsion nozzle 2e is to stop the transfer of the caps C in a state where the dividing devices 4, 5 are still stopped during the period that the injected flow of the respective nozzles becomes stable and the temperature of the warm water also reaches a predetermined temperature. Upon the startup of the respective nozzles, the injection pressure in the respective supply pipes rises drastically, and the warm water temperature is of a low state since the pipes and the like are also cold and the injected flow from the respective nozzles is unstable. If the dividing devices 4, 5 resume their operation in the above state, the caps C are sterilized and cleaned in an unstable state while being transferred and, consequently, there may be cases where the inner surface and outer surface of the caps C cannot be sterilized and cleaned evenly under desirable conditions. Accordingly, upon the startup of the propulsion nozzles 2a, 2b, 2c, 2d, the reverse propulsion nozzle 2e is simultaneously operated to continue inhibiting the crammed state of the caps C, and the processing of steps S10 and S11 below is performed so as to stop the transfer of the caps C until the injected flow from the respective nozzles is stabilized.

In step S10, measurement information of the temperature, flow rate, and pressure of the sterilization-cleaning medium (warm water in this embodiment) is acquired from the temperature sensor, the flow sensor, and the pressure sensor, and, in step S11, whether the information of the sterilization-cleaning medium satisfies predetermined conditions is determined. When the predetermined conditions are satisfied (YES), the routine proceeds to step S12 (FIG. 9), and when the predetermined conditions are not satisfied, the routine returns to step S10 and repeatedly acquires the measurement information until the predetermined conditions are satisfied. Prior to proceeding from steps S11 to S12, preferably hold control is performed for refraining from proceeding to step S12 for a predetermined time using a timer in order to reliably guarantee the sterilization and cleaning of the 30 caps in the sterilization-cleaning chute portion.

Returning to FIG. 9 once again, in step S12, in preparation for resuming the cap transfer, the solenoid valve which is blocking the passage between the sterilization-cleaning liquid tank 10 and the reverse propulsion supply pipe 3e is turned OFF (closed), and the stop processing of the warm water injection from the reverse propulsion nozzle 2e is performed.

In step S13, the flow rate and pressure information related to the reverse propulsion nozzle 2e are acquired from the measurement signal of the flow sensor 9e not shown in the drawing and the measurement signal of the pressure sensor 8e provided to the reverse propulsion supply pipe 3e, and whether the reverse propulsion nozzle 2e has stopped is determined based on the information in subsequent step S14. When the reverse propulsion nozzle 2e is in a stopped state, since warm water is not flowing in the reverse propulsion supply pipe 3e, the command value of the flow sensor 9e is shown as zero, but there may be cases where the value does not show zero due to a measurement error. Moreover, the command value of the pressure sensor 8e shows a value that represents pressure that is substantially the same as the inner pressure of the chamber 7 in the measurement of the absolute pressure, or a value that represents pressure that is slightly higher than the inner pressure of the chamber due to the resistance of the nozzle. Thus, based on testing and the like, whether the injection of the reverse propulsion nozzle 2e has stopped is preferably determined based on whether a set value (or threshold) that was set regarding at least one of either the pressure or flow rate for determining the stoppage of the nozzle is satisfying the command value of the pressure sensor or the flow sensor.

When it is determined that the reverse propulsion nozzle 2e is stopped (YES), the routine proceeds to step S15, and the operation of the dividing devices 4, 5 is resumed. In addition, the "temporary stop processing of the cap sterilization-cleaning device" is ended and the routine returns to the main processing. When it is determined that the reverse propulsion nozzle 2e is not stopped (No), the routine returns to step S13, and the information acquisition and determination are repeated until the reverse propulsion nozzle 2e is stopped.

The "temporary stop processing of the cap sterilization-cleaning device" may be processed as a subroutine (function) from other processing such as the main processing as described above, or repeatedly executed and processed in the form of being embedded in the main processing or other processing.

As another control method of the reverse propulsion nozzle 2e, for example, rather than stopping the injection of the reverse propulsion nozzle 2e during normal operation or when a command for stopping the injection is given to the reverse propulsion nozzle 2e while the propulsion nozzles are injecting as shown in step S12 of FIG. 9, it is also possible to perform control so as to weaken the injected flow of the sterilization-cleaning liquid from the reverse propulsion nozzle 2e to a level that the caps can be sufficiently transferred by narrowing the aperture of a flow regulating valve (not shown in the drawing) or a pressure regulating valve (not shown in the drawing) provided between the sterilization-cleaning liquid tank 10 and the reverse propulsion supply pipe 3e, or weaken the injected flow of the sterilization-cleaning liquid from the reverse propulsion nozzle 2e to a level that the caps can be sufficiently transferred by switching the injection of the reverse propulsion nozzle 2e from a straight mode to a fan shape mode. Meanwhile, when an injection start command is given to the reverse propulsion nozzle 2e while the dividing devices 4, 5 are stopped (for example, step S2 of FIG. 9 or step S9 of FIG. 10), it is also possible to perform control to increase the force of the injected flow from the reverse propulsion nozzle 2e to a level that the accumulated pressure of the caps can be effectively inhibited by spreading the aperture of the flow regulating valve or pressure regulating valve, or increase the force of the injected flow from the reverse propulsion nozzle 2e to a level that the accumulated pressure of the caps can be effectively inhibited by switching the injection of the reverse propulsion nozzle 2e from a fan shape mode to a straight mode. However, even during the control, for instance, if a stop command is given to both the propulsion nozzles and the reverse propulsion nozzle 2e as shown in step S6 of FIG. 10, it is preferably to control the solenoid valves so as to also stop the injection of the reverse propulsion nozzle 2e.

As described above, according to the cap sterilization-cleaning device 100 of the present invention, it is possible to evenly sterilize and clean the inner and outer surfaces of the caps C by continuously injecting the sterilization-cleaning liquid from the plurality of propulsion nozzles 2a, 2b, 2c, 2d disposed along the chute transfer passage 1, and simultaneously obtain the propulsive force for transferring the caps without requiring a mechanical power mechanism, and, even in cases where the dividing devices 4, 5 as the cap sending mechanism are stopped, it is possible to favorably prevent the deformation of the caps C in the chute transfer passage 1 while continuing the sterilization-cleaning process by continuously injecting the sterilization-cleaning liquid from the propulsion nozzles 2a, 2b, 2c, 2d and additionally injecting the sterilization-cleaning liquid from the reverse propulsion nozzle 2e.

INDUSTRIAL APPLICABILITY

The cap sterilization-cleaning device of the present invention can be suitably applied to a sterilization-cleaning device for synthetic resin caps, metal caps or the like.

The invention claimed is:
1. A cap sterilization-cleaning method, comprising:
transferring a plurality of caps to be sprayed with a sterilization-cleaning liquid, in a cap transfer passage, the cap transfer passage including a chute and a dividing device disposed along a transfer direction of caps, and spraying the plurality of caps with the sterilization-cleaning liquid output from a propulsion nozzle and a reverse propulsion nozzle, wherein when stoppage of the dividing device is detected, the sterilization-cleaning liquid is sprayed from the reverse propulsion nozzle to the caps, in a direction opposite to the transfer direction of the caps, wherein the cap transfer passage and the reverse propulsion nozzle are configured such that the reverse propulsion nozzle is disposed so as to spray the sterilization-cleaning liquid toward an inner surface of the caps.

2. The cap sterilization-cleaning method according to claim 1, wherein the caps are transferred without a mechanical power mechanism.

* * * * *